(12) United States Patent
Doyen et al.

(10) Patent No.: US 11,756,200 B2
(45) Date of Patent: *Sep. 12, 2023

(54) MEDICAL IMAGING WITH FUNCTIONAL ARCHITECTURE TRACKING

(71) Applicant: Omniscient Neurotechnology Pty Limited, Sydney (AU)

(72) Inventors: Stephane Philippe Doyen, Glebe (AU); Michael Edward Sughrue, Sydney (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 31 days.

This patent is subject to a terminal disclaimer.

(21) Appl. No.: 17/481,855

(22) Filed: Sep. 22, 2021

(65) Prior Publication Data
US 2022/0265145 A1  Aug. 25, 2022

Related U.S. Application Data

(63) Continuation of application No. 17/180,556, filed on Feb. 19, 2021, now Pat. No. 11,147,454.

(51) Int. Cl.
| | |
|---|---|
| *G06K 9/00* | (2022.01) |
| *A61K 35/12* | (2015.01) |
| *G06T 7/00* | (2017.01) |
| *A61B 5/00* | (2006.01) |
| *G06N 20/00* | (2019.01) |
| *G06F 18/214* | (2023.01) |

(52) U.S. Cl.
CPC .......... *G06T 7/0016* (2013.01); *A61B 5/0042* (2013.01); *A61B 5/4064* (2013.01);
(Continued)

(58) Field of Classification Search
CPC .......... G06T 7/0012; G06K 9/00; A61B 5/00; A61K 35/12
(Continued)

(56) References Cited

U.S. PATENT DOCUMENTS 8,885,926 B2   11/2014   Seung et al.
9,265,441 B2 *  2/2016   Pereira ..................... G06T 7/11
(Continued)

FOREIGN PATENT DOCUMENTS

WO   WO 2020/048593   3/2020

OTHER PUBLICATIONS

International Search Report and Written Opinion in International Appln. No. PCT/AU2022/050029, dated Apr. 28, 2022, 10 pages.

*Primary Examiner* — Seyed H Azarian
(74) *Attorney, Agent, or Firm* — Fish & Richardson P.C.

(57) ABSTRACT

A pre-event connectome of a subject brain is accessed, the pre-event connectome defining i) first functional nodes in the subject brain and ii) first edges that represent connections between the first functional nodes before the subject has undergone an event. A post-event connectome of the subject brain is accessed, the post-event connectome defining i) second functional nodes in the subject brain and ii) second edges that represent connections between the second functional nodes after the subject has undergone the event. A connectome-difference map data is generated that records the difference between the pre-event connectome and the post-event connectome. An action is taken based on the connectome-difference map data.

18 Claims, 7 Drawing Sheets

(52) U.S. Cl.
CPC ........... G06F 18/214 (2023.01); G06N 20/00 (2019.01); G06T 7/0014 (2013.01); *G06T 2207/20081* (2013.01); *G06T 2207/30016* (2013.01)

(58) Field of Classification Search
USPC ....... 382/100, 103, 106, 128–134, 155, 168, 382/173, 181, 199, 219, 232, 254, 276, 382/286, 298, 312, 305; 600/378, 393, 600/340
See application file for complete search history.

(56) References Cited

U.S. PATENT DOCUMENTS

| | | | |
|---|---|---|---|
| 9,563,950 B2* | 2/2017 | Raj | .................... G06F 18/2415 |
| 9,741,114 B2 | 8/2017 | Varkuti | |
| 9,940,712 B2 | 4/2018 | Henry et al. | |
| 10,586,326 B2 | 3/2020 | Silbersweig et al. | |
| 10,874,340 B2 | 12/2020 | Rau et al. | |
| 2003/0174873 A1* | 9/2003 | Giger | .................... G06T 7/0012 |
| | | | 382/128 |
| 2014/0316248 A1 | 10/2014 | deCharms | |
| 2014/0335489 A1 | 11/2014 | deCharms | |
| 2015/0018664 A1 | 1/2015 | Pereira et al. | |
| 2016/0300352 A1 | 10/2016 | Raj | |
| 2019/0251450 A1* | 8/2019 | McIntosh | ................ G06N 3/049 |
| 2020/0033431 A1 | 1/2020 | Schlemper et al. | |
| 2020/0167694 A1* | 5/2020 | Pisner | .................... G06N 5/022 |
| 2020/0230413 A1 | 7/2020 | Madhavan et al. | |
| 2020/0310098 A1 | 10/2020 | Ince et al. | |
| 2021/0118138 A1 | 4/2021 | Sughrue et al. | |
| 2021/0118226 A1 | 4/2021 | Sughrue et al. | |

* cited by examiner

MEDICAL IMAGING WITH FUNCTIONAL ARCHITECTURE TRACKING

CROSS-REFERENCE TO RELATED APPLICATION

This application is a continuation of U.S. application Ser. No. 17/180,556, entitled "Medical Imaging with Functional Architecture Tracking" filed Feb. 19, 2021, contents of which is herein incorporated in its entirety.

TECHNICAL FIELD

This specification relates to medical imaging technology.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities.

SUMMARY

This specification describes technologies for creating a difference-map image showing changes to a brain's functional architecture. These technologies generally involve comparing a pre-event connectome of the brain to post-event connectome for the brain. A difference of the two connectomes is found that is topologically invariant, allowing this technology to function even when a portion of the brain is removed, causing a change in the shape of the brain.

In general, one innovative aspect of the subject matter described in this specification can be embodied in systems that one or more processors; and computer memory storing instructions that, when executed by the one or more processors, cause the one or more processors to perform operations. The operations include accessing a pre-event connectome of a subject brain, the pre-event connectome defining i) first functional nodes in the subject brain and ii) first edges that represent connections between the first functional nodes before the subject has undergone an event; accessing a post-event connectome of the subject brain, the post-event connectome defining i) second functional nodes in the subject brain and ii) second edges that represent connections between the second functional nodes after the subject has undergone the event; generating a connectome-difference map data that records the difference between the pre-event connectome and the post-event connectome; and taking an action based on the connectome-difference map data.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. The first functional nodes are the same nodes as the second functional nodes. The first functional nodes are a superset of the second functional nodes. The event is at least one of the group consisting of: a surgical removal of brain tissue, a traumatic brain injury, a behavioral intervention for the subject, advancement of a medical condition that causes cognitive decline, and learning by the subject. The operations further comprising imaging the subject before the event to generate pre-event brain image data; imaging the subject after the event to generate post-event brain image data; generating the pre-event connectome from the pre-event brain image data; and generating the post-event connectome from the post-event brain image data. A first functional node and a corresponding second functional node represent the same point of brain topology, and wherein the first functional node is in a first location in the skull of the subject and the second node is in a second location in the skull of the subject do to a change in brain physiology as part of the event. The operations further comprising rendering the connectome-difference map data with an image of the subject's brain having connections overlaid. The pre-event connectome and the post-event connectome are topologically invariant. The operations further comprising generation of a proposed therapy plan for the subject based on the connectome-difference map data. The operations further comprising generating a tagged connectome-difference map data that specifies both the connectome-difference map data and one or more cognitive changes. The operations further comprise adding the tagged connectome-difference map data to a dataset comprising other tagged connectome-difference map data; and training a machine-learning classifier using the dataset. The event is a first event and wherein the operations further comprising receiving a surgery plan for a second subject; determining that the surgery plan is a second event with at least a threshold similarity to the first event; and returning a report for the surgery plan that includes an assessment generated, at least in part, on the connectome-difference map data. The event is a disease and the operations further comprise generating a therapy recommendation based, at least in part, on the connectome-difference map data. The operations further comprising generating report-data that includes an explanation of a change in subject health caused by the event using the connectome-difference map data.

The subject matter described in this specification can be implemented in particular embodiments so as to realize one or more of the following advantages. The subject matter described in this specification advances medical imaging technology, e.g., the technologies of diagnostic assessments, therapeutic interventions, and neurosurgery. This technology allows for images to be created that show the effect of an event on the brain. The subject matter described in this specification can allow for new images useful in a variety of areas. This image can capture the effect of neurosurgical interventions that require the removal of brain tissue, causing a difference in shape of the brain. This technology can advantageously automatically account for the changes in shape and correctly show a change in the brain's connectome, even when the change in shape moves a functional node inside the brain of the patient. A difference-map image made possible by the subject matter described in this specification, and the difference-map from which the image is rendered may be used to advantageously drive a number of processes. For example, the connectome-difference map can be projected over an image of the subject's brain to aid in understanding the impact of the event. The connectome-difference map can be used as an input to a function to generate a proposed therapy plan for the subject, providing new and better therapy plans than would be available otherwise. The connectome-difference map can be used to generate automated data sets that describe a class of events, providing a deeper and more accurate data set than would be available otherwise. This technology can be useful in guiding surgeries, where for a specific patient a clinician can learn of deficient networks where little harm will be done and effective networks worth avoiding and preserving. Patterns of change in the difference image can be used to identify and classify specific disease states, including Alzheimer's as one example. Recovery over time can be monitored for a specific patient, instead of relying on estimated recovery timelines. The effectiveness of particular treatments for particular patients can be monitored.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

The subject matter described in this specification can subtract a connectome generated for a subject's brain before an event from a connectome generated for the same brain after the brain has undergone one or more events that can cause a change to the brains functional architecture. In this way, the impact of the event on the subject can be recorded and/or visualized into new kinds of images, and/or used as inputs for new types of computational processes able to produce new and useful outputs not previously possible. These outputs may be useful alone, or may be useful when combined with human actions. For example, a surgeon that would otherwise plan a surgery based on intuition and training can be informed using the subject matter described in this specification to generate a surgical-plan assessment based on historic, and objective, data collection and processing.

Figure 1A:
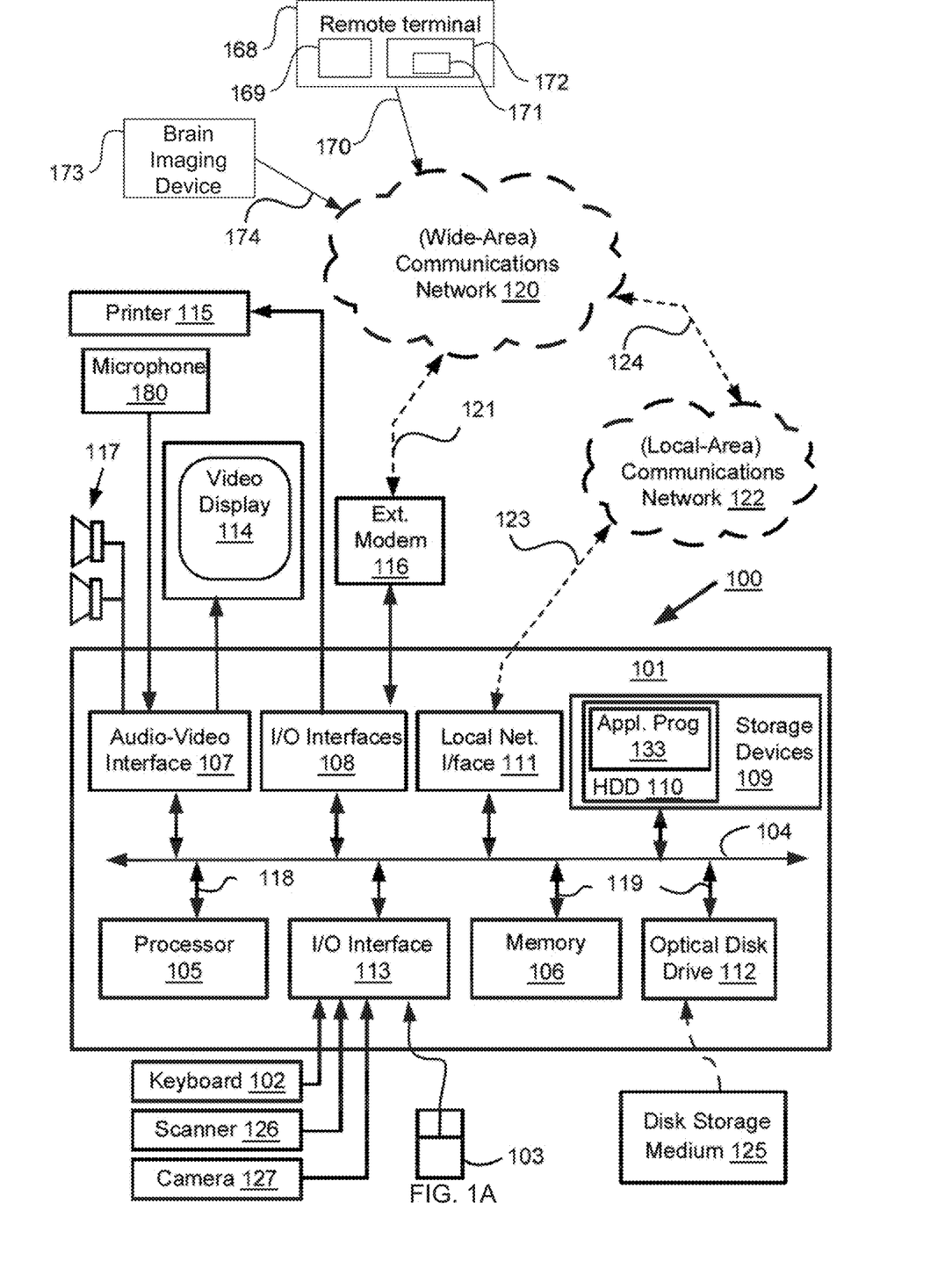
FIGS. 1A and 1B show an example computer system.
Figure 1B:
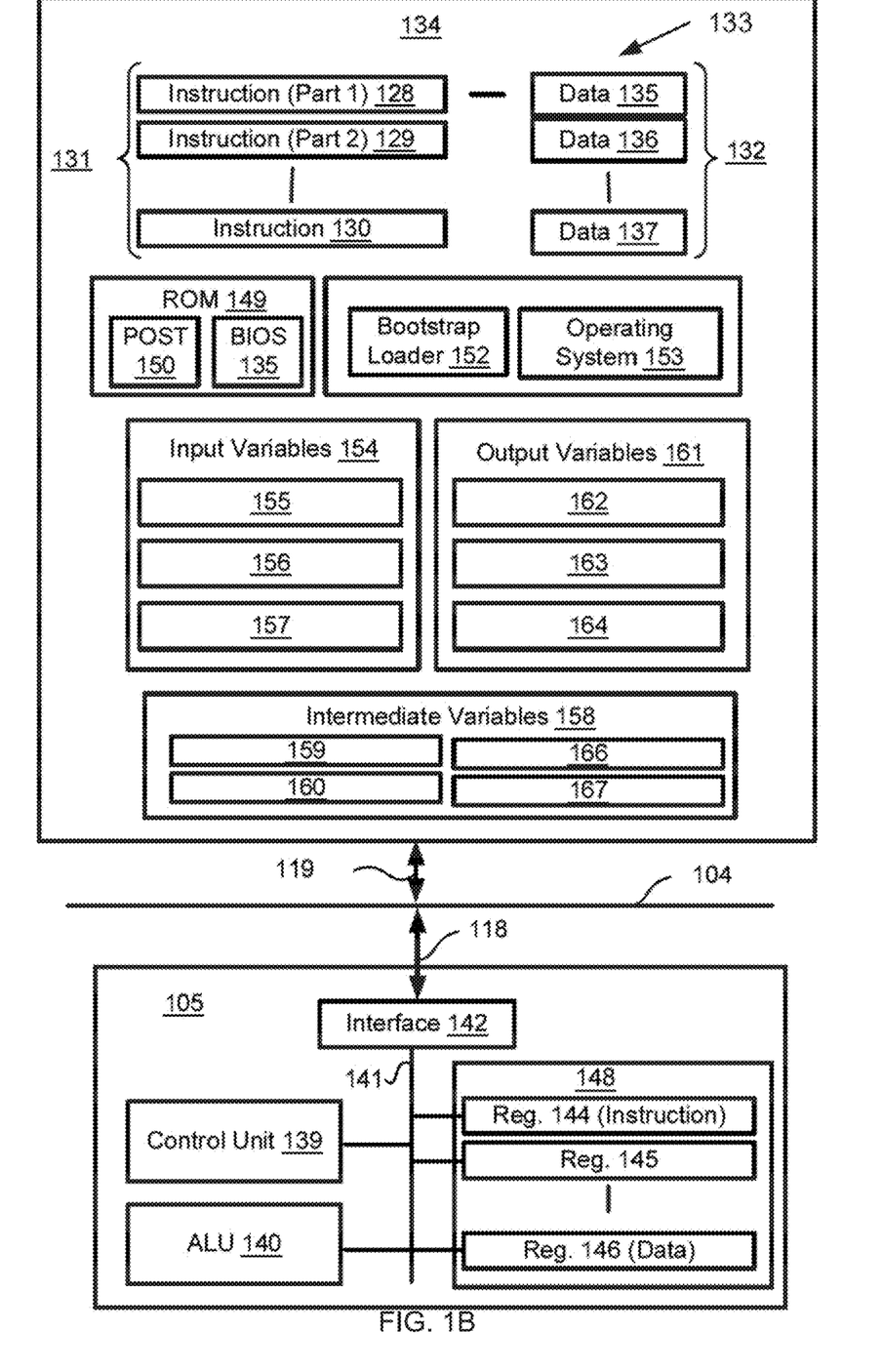

FIGS. 1A and 1B are block diagrams of a general-purpose computer system 100 upon which one can practice arrangements described in this specification. The following description is directed primarily to a computer server module 101. However, the description applies equally or equivalently to one or more remote terminals 168.

As seen in FIG. 1A, the computer system 100 includes: the server computer module 101; input devices such as a keyboard 102, a pointer device 103 (e.g., a mouse), a scanner 126, a camera 127, and a microphone 180; and output devices including a printer 115, a display device 114 and loudspeakers 117. An external Modulator-Demodulator (Modem) transceiver device 116 may be used by the computer server module 101 for communicating to and from the remote terminal 168 over a computer communications network 120 via a connection 121 and a connection 170. The aforementioned communication can take place between the remote terminal 168 and "the cloud" which in the present description comprises at least the one server module 101. The remote terminal 168 typically has input and output devices (not shown) which are similar to those described in regard to the server module 101. The communications network 120 may be a wide-area network (WAN), such as the Internet, a cellular telecommunications network, or a private WAN. Where the connection 121 is a telephone line, the modem 116 may be a traditional "dial-up" modem. Alternatively, where the connection 121 is a high capacity (e.g., cable) connection, the modem 116 may be a broadband modem. A wireless modem may also be used for wireless connection to the communications network 120.

The computer server module 101 typically includes at least one processor unit 105, and a memory unit 106. For example, the memory unit 106 may have semiconductor random access memory (RAM) and semiconductor read only memory (ROM). The remote terminal 168 typically includes as least one processor 169 and a memory 172. The computer server module 101 also includes a number of input/output (I/O) interfaces including: an audio-video interface 107 that couples to the video display 114, loudspeakers 117 and microphone 180; an I/O interface 113 that couples to the keyboard 102, mouse 103, scanner 126, camera 127 and optionally a joystick or other human interface device (not illustrated); and an interface 108 for the external modem 116 and printer 115. In some implementations, the modem 116 may be incorporated within the computer module 101, for example within the interface 108. The computer module 101 also has a local network interface 111, which permits coupling of the computer system 100 via a connection 123 to a local-area communications network 122, known as a Local Area Network (LAN). As illustrated in FIG. 1A, the local communications network 122 may also couple to the wide network 120 via a connection 124, which would typically include a so-called "firewall" device or device of similar functionality. The local network interface 111 may include an Ethernet circuit card, a Bluetooth® wireless arrangement or an IEEE 802.11 wireless arrangement; however, numerous other types of interfaces may be practiced for the interface 111.

The I/O interfaces 108 and 113 may afford either or both of serial or parallel connectivity; the former may be implemented according to the Universal Serial Bus (USB) standards and having corresponding USB connectors (not illustrated). Storage memory devices 109 are provided and typically include a hard disk drive (HDD) 110. Other storage devices such as a floppy disk drive and a magnetic tape drive (not illustrated) may also be used. An optical disk drive 112 is typically provided to act as a non-volatile source of data. Portable memory devices, such optical disks (e.g., CD-ROM, DVD, Blu-ray Disc™), USB-RAM, portable, external hard drives, and floppy disks, for example, may be used as appropriate sources of data to the system 100.

The components 105 to 113 of the computer module 101 typically communicate via an interconnected bus 104 and in a manner that results in a conventional mode of operation of the computer system 100 known to those in the relevant art. For example, the processor 105 is coupled to the system bus 104 using a connection 118. Likewise, the memory 106 and optical disk drive 112 are coupled to the system bus 104 by connections 119.

The techniques described in this specification may be implemented using the computer system 100, e.g., may be implemented as one or more software application programs 133 executable within the computer system 100. In some implementations, the one or more software application programs 133 execute on the computer server module 101 (the remote terminal 168 may also perform processing jointly with the computer server module 101), and a browser 171 executes on the processor 169 in the remote terminal, thereby enabling a user of the remote terminal 168 to access the software application programs 133 executing on the server 101 (which is often referred to as "the cloud") using the browser 171. In particular, the techniques described in this specification may be effected by instructions 131 (see FIG. 1B) in the software 133 that are carried out within the computer system 100. The software instructions 131 may be formed as one or more code modules, each for performing one or more particular tasks. The software may also be divided into two separate parts, in which a first part and the corresponding code modules performs the described techniques and a second part and the corresponding code modules manage a user interface between the first part and the user.

The software may be stored in a computer readable medium, including the storage devices described below, for example. The software is loaded into the computer system 100 from the computer readable medium, and then executed by the computer system 100. A computer readable medium having such software or computer program recorded on the computer readable medium is a computer program product. Software modules for that execute techniques described in this specification may also be distributed using a Web browser.

The software 133 is typically stored in the HDD 110 or the memory 106 (and possibly at least to some extent in the memory 172 of the remote terminal 168). The software is loaded into the computer system 100 from a computer readable medium, and executed by the computer system 100. Thus, for example, the software 133, which can include one or more programs, may be stored on an optically readable disk storage medium (e.g., CD-ROM) 125 that is read by the optical disk drive 112. A computer readable medium having such software or computer program recorded on it is a computer program product.

In some instances, the application programs 133 may be supplied to the user encoded on one or more CD-ROMs 125 and read via the corresponding drive 112, or alternatively may be read by the user from the networks 120 or 122. Still further, the software can also be loaded into the computer system 100 from other computer readable media. Computer readable storage media refers to any non-transitory tangible storage medium that provides recorded instructions and/or data to the computer system 100 for execution and/or processing. Examples of such storage media include floppy disks, magnetic tape, CD-ROM, DVD, Blu-Ray™ Disc, a hard disk drive, a ROM or integrated circuit, USB memory, a magneto-optical disk, or a computer readable card such as a PCMCIA card and the like, whether or not such devices are internal or external of the computer module 101. Examples of transitory or non-tangible computer readable transmission media that may also participate in the provision of software, application programs, instructions and/or data to the computer module 101 include radio or infra-red transmission channels as well as a network connection to another computer or networked device, and the Internet or Intranets including e-mail transmissions and information recorded on Websites and the like.

The second part of the application programs 133 and the corresponding code modules mentioned above may be executed to implement one or more graphical user interfaces (GUIs) to be rendered or otherwise represented upon the display 114. For example, through manipulation of the keyboard 102 and the mouse 103, a user of the computer system 100 and the application may manipulate the interface in a functionally adaptable manner to provide controlling commands and/or input to the applications associated with the GUI(s). Other forms of functionally adaptable user interfaces may also be implemented, such as an audio interface utilizing speech prompts output via the loudspeakers 117 and user voice commands input via the microphone 180.

FIG. 1B is a detailed schematic block diagram of the processor 105 and a "memory" 134. The memory 134 represents a logical aggregation of all the memory modules (including the HDD 109 and semiconductor memory 106) that can be accessed by the computer module 101 in FIG. 1A.

When the computer module 101 is initially powered up, a power-on self-test (POST) program 150 can execute. The POST program 150 can be stored in a ROM 149 of the semiconductor memory 106 of FIG. 1A. A hardware device such as the ROM 149 storing software is sometimes referred to as firmware. The POST program 150 examines hardware within the computer module 101 to ensure proper functioning and typically checks the processor 105, the memory 134 (109, 106), and a basic input-output systems software (BIOS) module 151, also typically stored in the ROM 149, for correct operation. Once the POST program 150 has run successfully, the BIOS 151 can activate the hard disk drive 110 of FIG. 1A. Activation of the hard disk drive 110 causes a bootstrap loader program 152 that is resident on the hard disk drive 110 to execute via the processor 105. This loads an operating system 153 into the RAM memory 106, upon which the operating system 153 commences operation. The operating system 153 is a system level application, executable by the processor 105, to fulfil various high-level functions, including processor management, memory management, device management, storage management, software application interface, and generic user interface.

The operating system 153 manages the memory 134 (109, 106) to ensure that each process or application running on the computer module 101 has sufficient memory in which to execute without colliding with memory allocated to another process. Furthermore, the different types of memory available in the system 100 of FIG. 1A must be used properly so that each process can run effectively. Accordingly, the aggregated memory 134 is not intended to illustrate how particular segments of memory are allocated (unless otherwise stated), but rather to provide a general view of the memory accessible by the computer system 100 and how such is used.

As shown in FIG. 1B, the processor 105 includes a number of functional modules including a control unit 139, an arithmetic logic unit (ALU) 140, and a local or internal memory 148, sometimes called a cache memory. The cache memory 148 typically includes a number of storage registers 144-146 in a register section. One or more internal busses 141 functionally interconnect these functional modules. The processor 105 typically also has one or more interfaces 142 for communicating with external devices via the system bus 104, using a connection 118. The memory 134 is coupled to the bus 104 using a connection 119.

The application program 133 includes a sequence of instructions 131 that may include conditional branch and loop instructions. The program 133 may also include data 132 which is used in execution of the program 133. The instructions 131 and the data 132 are stored in memory locations 128, 129, 130 and 135, 136, 137, respectively. Depending upon the relative size of the instructions 131 and the memory locations 128-130, a particular instruction may be stored in a single memory location as depicted by the instruction shown in the memory location 130. Alternately, an instruction may be segmented into a number of parts each of which is stored in a separate memory location, as depicted by the instruction segments shown in the memory locations 128 and 129.

In general, the processor 105 is given a set of instructions which are executed therein. The processor 105 waits for a subsequent input, to which the processor 105 reacts to by executing another set of instructions. Each input may be provided from one or more of a number of sources, including data generated by one or more of the input devices 102, 103, data received from an external source 173, e.g., a brain imaging device 173 such as an MRI or DTI scanner, across one of the networks 120, 122, data retrieved from one of the storage devices 106, 109 or data retrieved from a storage medium 125 inserted into the corresponding reader 112, all depicted in FIG. 1A. The execution of a set of the instructions may in some cases result in output of data. Execution may also involve storing data or variables to the memory 134.

Some techniques described in this specification use input variables 154, e.g., data sets characterizing the brain of a patient, which are stored in the memory 134 in corresponding memory locations 155, 156, 157. The techniques can produce output variables 161, which are stored in the memory 134 in corresponding memory locations 162, 163, 164. Intermediate variables 158 may be stored in memory locations 159, 160, 166 and 167.

Referring to the processor 105 of FIG. 1B, the registers 144, 145, 146, the arithmetic logic unit (ALU) 140, and the control unit 139 work together to perform sequences of micro-operations needed to perform "fetch, decode, and execute" cycles for every instruction in the instruction set making up the program 133. Each fetch, decode, and execute cycle can include i) a fetch operation, which fetches or reads an instruction 131 from a memory location 128, 129, 130; ii) a decode operation in which the control unit 139 determines which instruction has been fetched; and iii) an execute operation in which the control unit 139 and/or the ALU 140 execute the instruction.

Thereafter, a further fetch, decode, and execute cycle for the next instruction may be executed. Similarly, a store cycle may be performed by which the control unit 139 stores or writes a value to a memory location 132.

Each step or sub-process in the techniques described in this specification may be associated with one or more segments of the program 133 and is performed by the register section 144, 145, 146, the ALU 140, and the control unit 139 in the processor 105 working together to perform the fetch, decode, and execute cycles for every instruction in the instruction set for the noted segments of the program 133. Although a cloud-based platform has been described for practicing the techniques described in this specification, other platform configurations can also be used. Furthermore, other hardware/software configurations and distributions can also be used for practicing the techniques described in this specification.

Figure 2:
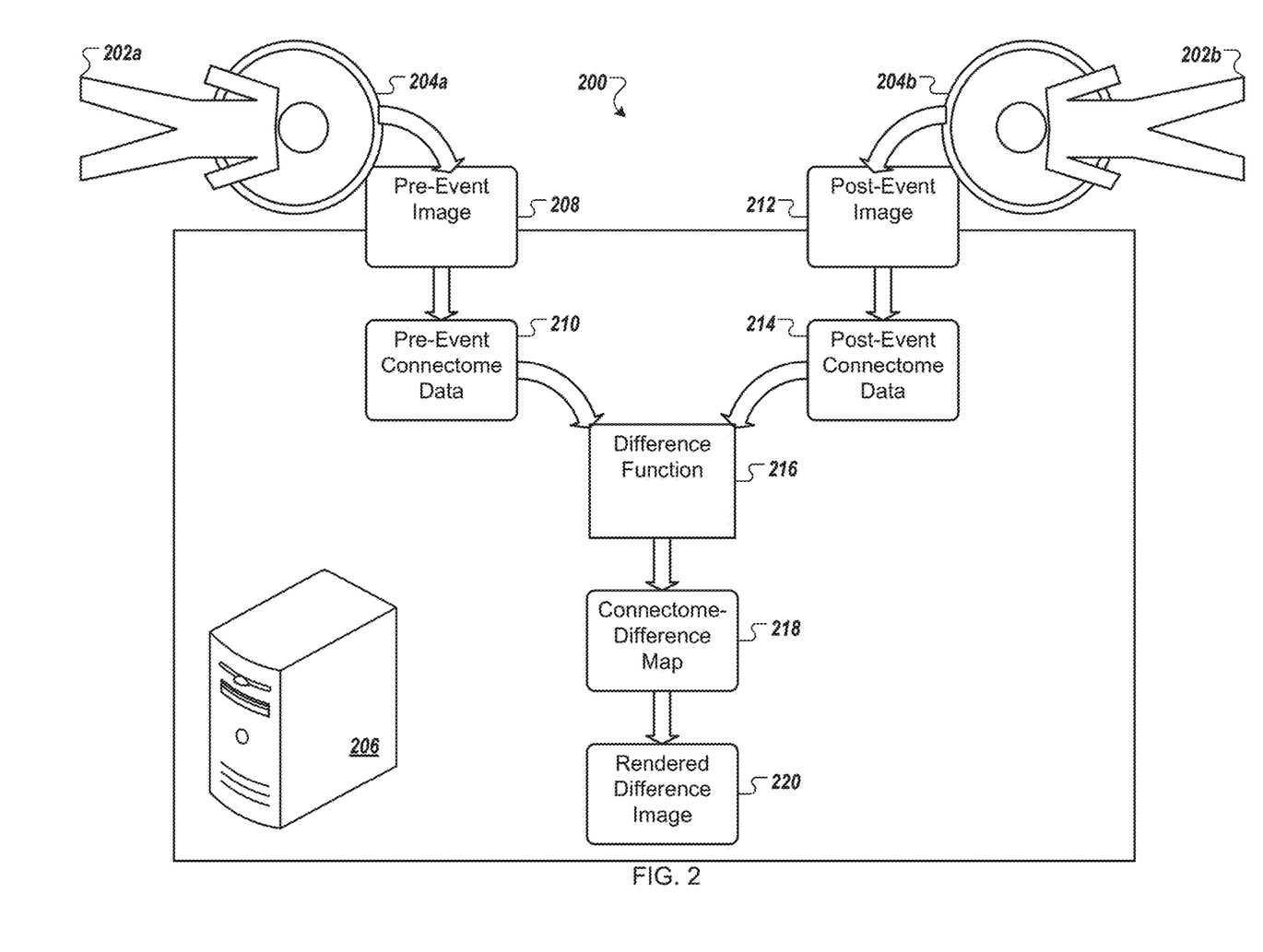
FIG. 2 shows an example system for generating medical images with connectome-difference map generation.

FIG. 2 shows an example system 200 for generating medical images with connectome-difference map generation. In the system 200, a medical imager 202 images a subject 204 before and after an event, or a second medical imager (not shown) may be used, and provides data from the imaging to computing apparatus 206 for processing and storage, e.g., across one or more networks.

The medical imager 202 represents any sort of device that generates medical images, including images that are only stored as binary (or similar) data and never rendered into a graphical format. Examples include functional magnetic resonance imaging (fMRI) machines, magnetic resonance imaging MRI machines, and computed tomography machines. At a first time, the subject 202 (shown as 202a at the first time) is imaged by the medical imager 204 (shown as 204a at the first time) to generate pre-event image data 208. At a later time after the subject has undergone an event, the subject (shown as 202b at the later time) is imaged by the same imager 204 (shown as 204b at the later time) or another imager (not shown) to generate post-event image data 212. As will be appreciated, the pre-event image 208 may be not have been gathered with the intention of being used as a pre-event image as described here. For example, a medical patient may receive imaging for one reason, then later suffer an unexpected brain injury. The previous image data may then be used as the pre-event (i.e. pre-brain injury) image 208.

The pre-event image 208 can be processed by apparatus 206 into pre-event connectome data 210. The post-event image 212 can be processed by apparatus 206 into post-event connectome data 214. For example, time series activity can be processed to produce a connectivity correlation matrix arranged by voxel. These voxels can be grouped to produce group parcellation connectomes. Examples of such processing can be found, for example, in U.S. application Ser. Nos. 17/066,171 and 17/066,178, the contents of which are hereby incorporated by reference.

Apparatus 206 can execute a difference function to generate a connectome difference map 218 from the pre-event connectome data 210 and the post-event connectome data 214. For example, the connectome data 210 and 214 may be stored on disk in a data structure useful for storing directed or undirected graphs containing nodes and edges. This can include a connectivity matrix, a list of all edges, or hash tables with indexes of the nodes and pointing to linked lists of other nodes connected to the indexed node, to name a few. As will be understood, the map 218 may be stored on disk as a collection of binary values, and those binary values can be interpreted by apparatus 206. This map 218 may be used as input data for other functions, and/or may be rendered into one or more rendered difference images 220. For example, apparatus 206 can use the map 218 to generate a displayable image (e.g., a JPEG) or interactive interface that shows a two-dimensional matrix with cells shaded to show corresponding edges displayed in the map 218, and render a visual representation of the brain (e.g. the pre-event image 208, the post-event image 212, or a default brain image) with edges of the map 218 superimposed over the brain. See, for example, FIG. 3.

As will be appreciated, the speed and scale of data generated in such processes may be quite significant, and producing results in clinically-useful time-frames may require the use of data pro-processing, efficient data networking technologies, and data storage techniques. For example, the pre-event image 208 and post-event image 212 can both require an hour or hours of processing time each to produce the data 210 and 214 when using consumer, off the shelf computing products. When faster speed is required, more advanced processing may be accessed via cloud-provided computational resources. Accessing such resources provides advantages of producing rendered images 220 in shorter timescales. Which time is a critical factor (e.g., a patient awaiting emergency surgery), slower processing by slower machines or human computation may not provide the advantage due to the size and scale of the processing described here.

Figure 3:
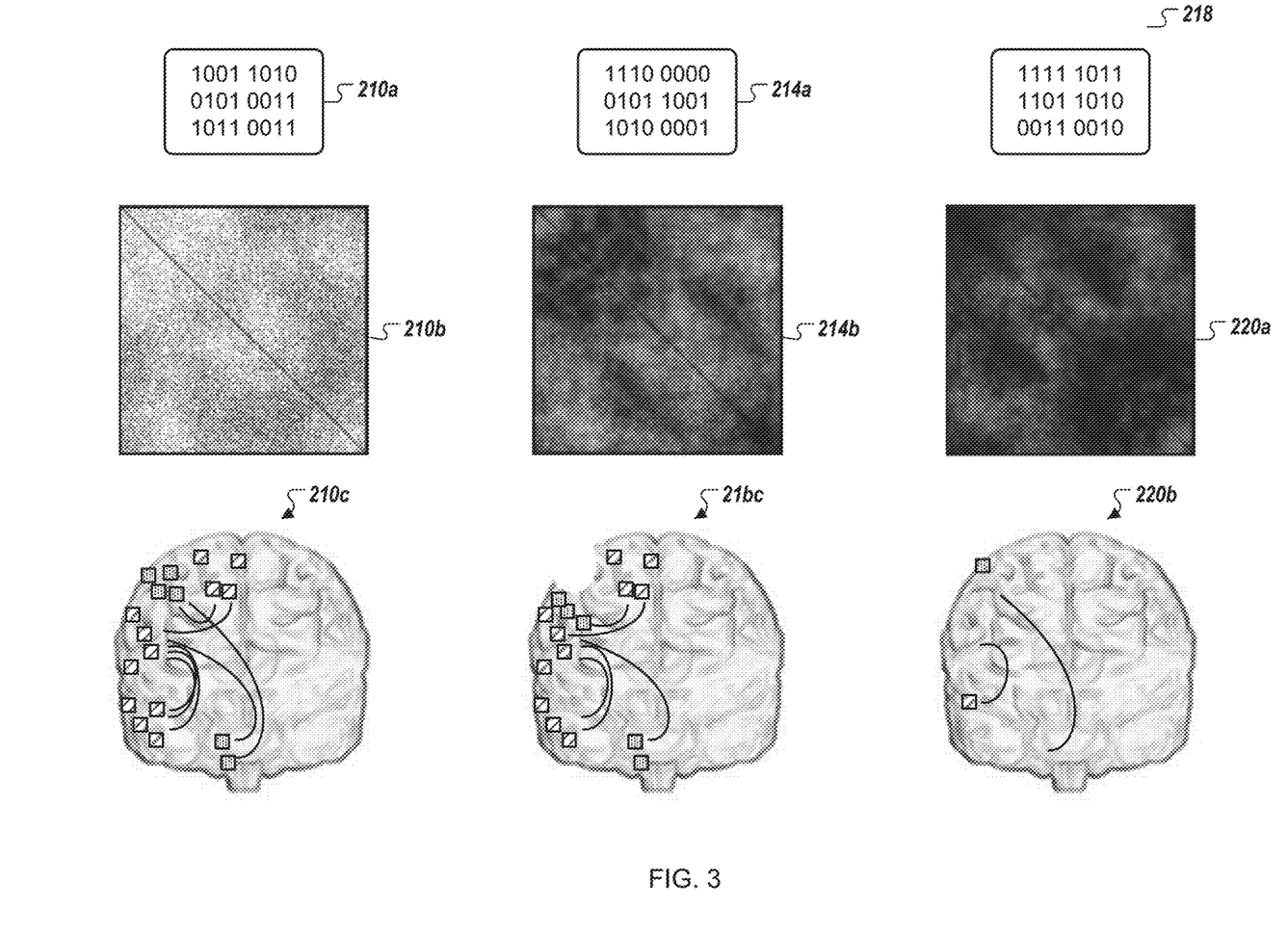
FIG. 3 shows an example of data generated by medical imaging.

FIG. 3 shows an example of data generated by medical imaging. Shown here are three views of the pre-event connectome data 210, the post event connectome data 214, and the connectome difference map 218 (including two examples of the rendered difference image 220).

As will be understood the pre-event connectome data 210, the post event connectome data 214, and the connectome difference map 218 can be stored on disk as binary digits 210a, 214a, 218. In addition, the binary digits 210a, 214a, 218 can be loaded into a processor for computation, transmitted over computer networks, compressed, copied, etc.

In some instances, apparatus 206 can interpret the binary digits 210a, 214a, and 218 as structured data. For example, apparatus 206 can interpret the binary digits 210a as the pre-event connectome 210. The pre-event connectome data can include data 210 defining i) first functional nodes in the subject brain and ii) first edges that represent connections between the first functional nodes before the subject has undergone an event. This data may be stored in any suitable data structure for storing and accessing such data, including but not limited to an adjacency matrix stored in a .csv file.

In some instances, apparatus 206 can interpret the binary digits 214a as the post-event connectome 214. This post-event connectome data can include data 214 defining i) second functional nodes in the subject brain and ii) second edges that represent connections between the second functional nodes after the subject has undergone the event. This data may be stored in any suitable data structure for storing and accessing such data, including but not limited to an adjacency matrix.

In some cases, each node may map 2-to-1 to each parcellation in a parcellation scheme of the brain. However, other arrangements are possible. For example, a node may represent groups of parcellation schemes. This may be desirable when less detailed information is useful for a particular purpose (e.g., showing a rendering at a readable resolution may not require as much detailed connectome data). However, for some other uses (e.g., machine-learning data generation) the higher-detail 2-to-1 mapping may be more beneficial.

In some cases, the pre-event connectome 210 and the post-event connectome 214 are topologically invariant. As will be understood, brain function is tied to the two-dimensional topology (i.e. surface shape) of the brain, but not to the underlying three-dimensional morphology of the brain. Some events can change brain morphology (e.g., removal of a tumor, some traumatic injuries), which may have topological changes (changes to the two-dimensional surface of the brain) as well as non-topological changes (changes that do not change the two-dimensional surface of the brain. However, these non-topological changes can influence the location in three-dimensional space within the subject's skull, in which a given point of topology resides. For example, removal of a tumor may cause the surrounding brain tissue to sag, maintaining the same topology but in a new location in the skull.

A first functional node in the pre-event connectome 210 and a corresponding second functional node in the post-event connectome 214 can represent the same point of brain topology. When the morphological change occurs without changing the node at issue, the first functional node is in a first location in the skull of the subject and the second node is in a second location in the skull of the subject due to a change in brain physiology as part of the event. This location may vary in space as a tumor can change the volume of the brain, or plasticity can re-assign brain tissue to other functions As such, the pre-event connectome 210 and the post-event connectome 214 are topologically invariant. For example, a node in the pre-event connectome 210 can have the same topological location as the corresponding node in the post-event connectome data 214. This ensure that the connectomes are tied to areas (e.g., parcellations) on the topology in order to preserve functional features of the brain pre and post, for example, sagging.

In the pre-event connectome 210 and the post-event connectome 214, the first functional nodes may be the same nodes as the second functional nodes. For example, a given event may not change the topology of the brain, and may or may not change the functional connections between parcellations (represented by the nodes in the data 210 and 214). An event that has no effect, then, could produce an identical or nearly identical pre- and post-connectome 210 and 214. As will be understood, the volume of data at issue, the noise in the imaging, and biological functions can influence these processes such that two imaging for the exact same brain, one after another, will not be likely to be the same, digit for digit.

In other cases, the first function nodes may be different than the second functional nodes. For example, the first functional nodes may be a superset of the second functional nodes. This may be the case when functional nodes are removed or destroyed by the event. In some examples, the first function nodes may be a subset of the second functional nodes. This may be the case when functional nodes are created by the event. In some cases, the first and second function nodes may be a partly overlapping set, such as when some nodes are created and some destroyed. Events that can change the nodes in the brain include, but are not limited to, tissue growth, spontaneous replacement, therapeutic replacement, traumatic damage, surgical intervention, and learning. As will be appreciated, the event may not necessarily be known or expected by clinicians or subjects. For example, this technology can be used for routine imaging and processed, and when significant changes are found, an alert can be generated. This can be used to alert the clinician and the patient of a potential issue much earlier than would otherwise be possible.

The connectome-difference map 212 records the difference between the pre-event connectome 210 and the post-event connectome 214. For example, the connectome-difference map 212 can record edges that appear or disappear between the pre- and post-event connectome data 210 and 214, and may also record changes in weight or one or more edges representing connections between the nodes (e.g., parcellations). In instances where a node is destroyed by the event, the edges between that node and other nodes may disappear. However, that is not the only possible change caused by the event. The event may also, or instead, strengthen or weaken the connection between two nodes, and this change in intensity can be found by finding the difference between edge weights pre- and post-.

Renderings 210b, 210c, 214b, 214c, 220a, and 220b show example rendering of the data 210a, 214a, and 218. As will be appreciated, the data stored on disk may be rendered by apparatus 206 into various useful visual appearances. The renderings 210b, 214b, and 220a show connectivity matrixes each containing a two-dimensional grid with color values and/or hues that represent the weight of edges in the corresponding data 210a, 214a, and 218. Renderings 210c, 214c, and 220b show (at least a subset) of the edges superimposed over a rendering of a brain, with the edges terminating at points in the topology matching the locations of the nodes the edges connect. It will be understood that other forms of renderings may be used.

Figure 4:
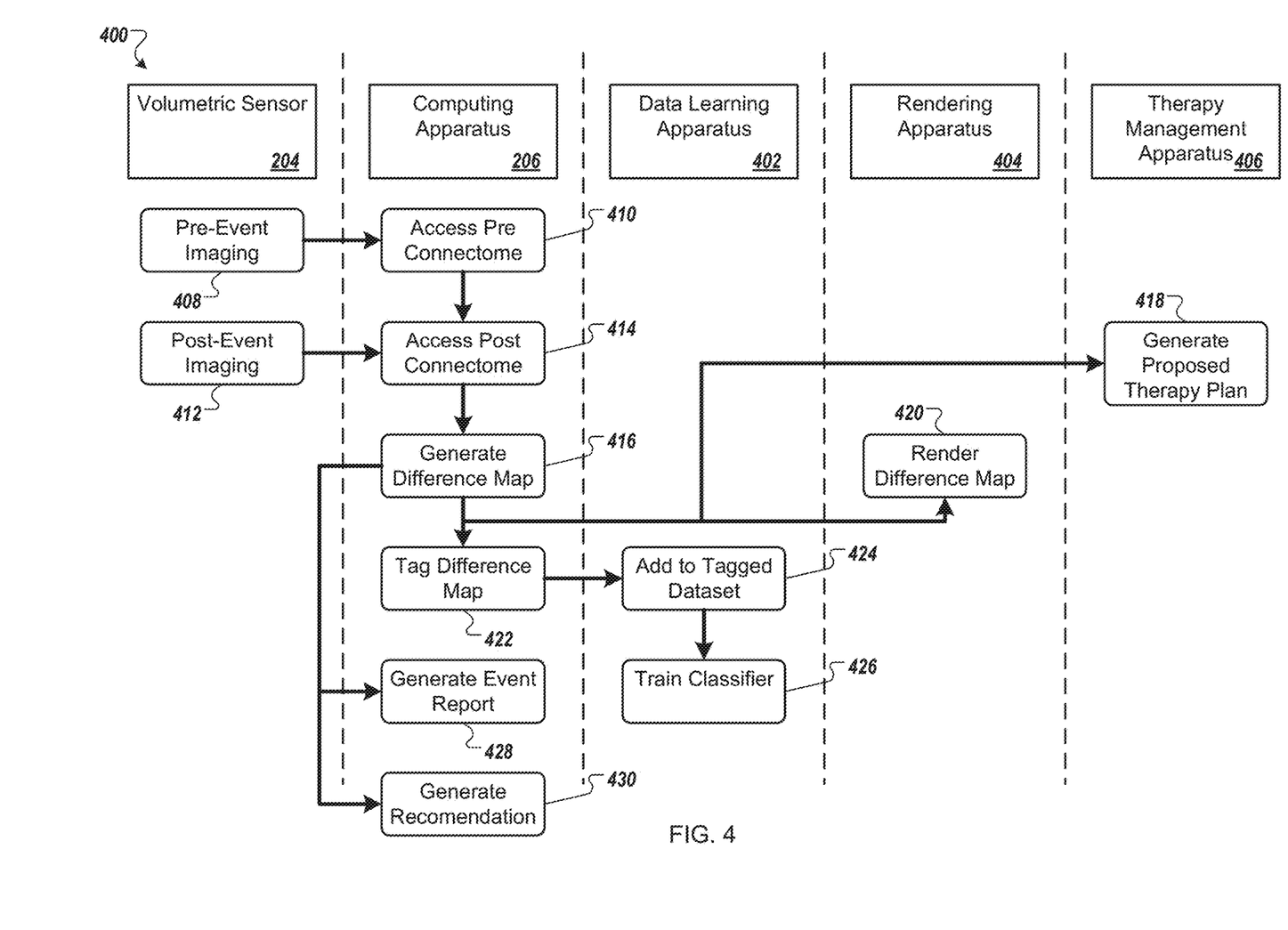
FIG. 4 shows an example process of a connectome-difference map being generated and used.

FIG. 4 shows an example process 400 of a connectome-difference map being generated and used. In the process 400, computing apparatus 206 generates a difference map from two images of a brain, and then the difference map is used for a number of uses. As will be understood, other processes may use difference maps for the same, fewer, more, and different uses. Other systems may perform the process 400 or other processes.

Pre-event imaging is performed 408. For example, the volumetric sensor 204 can perform one or more fMIR scans of a subject brain to image the subject before an event to generate a pre-event brain image. In this example, the subject is a medical patient preparing to undergo surgery to remove a brain tumor, and thus the description will continue with this example. However, the process 400 can be used for other purposes, including in both therapeutic and non-therapeutic contexts. Example events can include, but are not limited to, a surgical removal of brain tissue, a traumatic brain injury, a behavioral intervention for the subject, advancement of a medical condition that causes cognitive decline, and learning by the subject.

A pre-event connectome of the subject brain is accessed 410. For example, computing apparatus 206 can receive the fMRI data from the volumetric scanner 204 and can generate, from the fMRI data, a connectome of patient's brain before the surgery removes the tumor.

Post-event imaging is performed 412. For example, the volumetric sensor 204 can image the subject after the event to generate a post-event brain image. This can include performing one or more fMRI scans of the patient's brain after the tumor has been surgically removed, either with or without a delay to allow time for the patient to recover and heal from surgery. In some cases, delays for healing can be useful reduction of oedema/swelling post surgery.

A post-event connectome of the subject brain is accessed 414. For example, computing apparatus 206 can receive the fMRI data from the volumetric scanner 204 and can generate, from the fMRI data, a connectome of patient's brain after the surgery removes the tumor.

A connectome-difference map is generated 416. For example, computing apparatus 206 can compare the pre-event connectome to the post-event connectome and generate a record of differences between the two connectomes. This connectome-difference, generally speaking, represents the change to the functionality of the brain due to the event (and possibly any other intervening activity such as healing, occupational therapy after a surgery, pharmacological interventions cotemporaneous with the surgery, unrelated learning).

With the connectome-difference map, one or more useful processes can be performed. The following example will list some such useful processes, but it will be appreciated that others are possible.

A proposed therapy plan can be generated for the subject based on the connectome-difference map 418. For example, therapy management apparatus 406, with or without user direction, can access the connectome-difference map and create, terminate, or alter a proposed therapy plan for the subject based on data in the connectome-difference map not previously available. This proposal can include proposals for therapy plans that include prescribing pharmacological interventions, referring to occupational or physical therapy, modifying an existing treatment, starting a new treatment, or ending an existing treatment.

The connectome-difference map can be rendered 420 with an image of the subject's brain having connections overlaid. As previously described, there are multiple ways to render a connectome-difference map. Rendering apparatus 404 can render the difference map overlaid with the brain to aid in understanding of the impact of the event. For example, a clinician can show such a rendering to a patient to help explain the impact of the event; answer questions about the effects of the event; show why particular functions may or may not have been impaired, enhanced, or changed; etc. This rendering can be overlaid over the brain pre-event, post-event, or both. This can help show the context in which the functional changes take place—if many difference were found near a tumor, pre-and-post overlays can help show why those functions may have been impacted.

A tagged connectome-difference map that specifies both the connectome-difference map and one or more cognitive changes, the tagged connectome-difference map can be added to a dataset comprising other tagged connectome-difference maps 424; and a machine-learning classifier using the dataset can be trained 426. For example, data learning apparatus 402 can train machine-learning classifiers. By accessing the difference map tagged with cognitive changes (or any other outcomes of the event), datasets of functional changes can be created. With such datasets, machine-learning classifiers can be generated to aid in, for example, the classifications of events, physiological changes to the brain, connectome differences, etc. One example type of classifier to be used include boosted tree classifiers. In such a case, ensemble classifiers are trained by building regression trees in a step-wise fashion, using a predetermined loss function to measure error between an in-training model and the tagging provided for the difference maps. For example, each step of the step-wise process can add and weigh an addition function to an ensemble of functions in order to lower the result of the loss function.

Report-data that includes an explanation of a change in subject health caused by the event can be generated using the connectome-difference map 428. For example, computing apparatus 206 can access, with or without user direction, a report-template data object that includes a number of fields to be completed. Apparatus 206 can complete these fields with data of the connectome-difference map, data derived from the connectome-difference map (e.g., aggregate statistics, classifications of the differences based on classification of previously-described machine-learning classifiers), and from other data (e.g., patient name, date information). This report-data can be provided to the patient, sent to a caregiver of the patient, stored in an electronic-medical-records management system, etc.

A recommendation for a potential condition can be generated based, at least in part, on the connectome-difference map 430. For example, with an event that is a disease (e.g., normal pressure hydrocephalus, Lewis Body dementia, Alzheimer's disease, Pick's disease, or Creutzfeldt-Jakob disease), the connectome-difference map can be used to identify changes due to the disease, therapies used to treat the disease, etc. This can provide useful information to clinicians, care-givers, and disease researchers.

Figure 5:
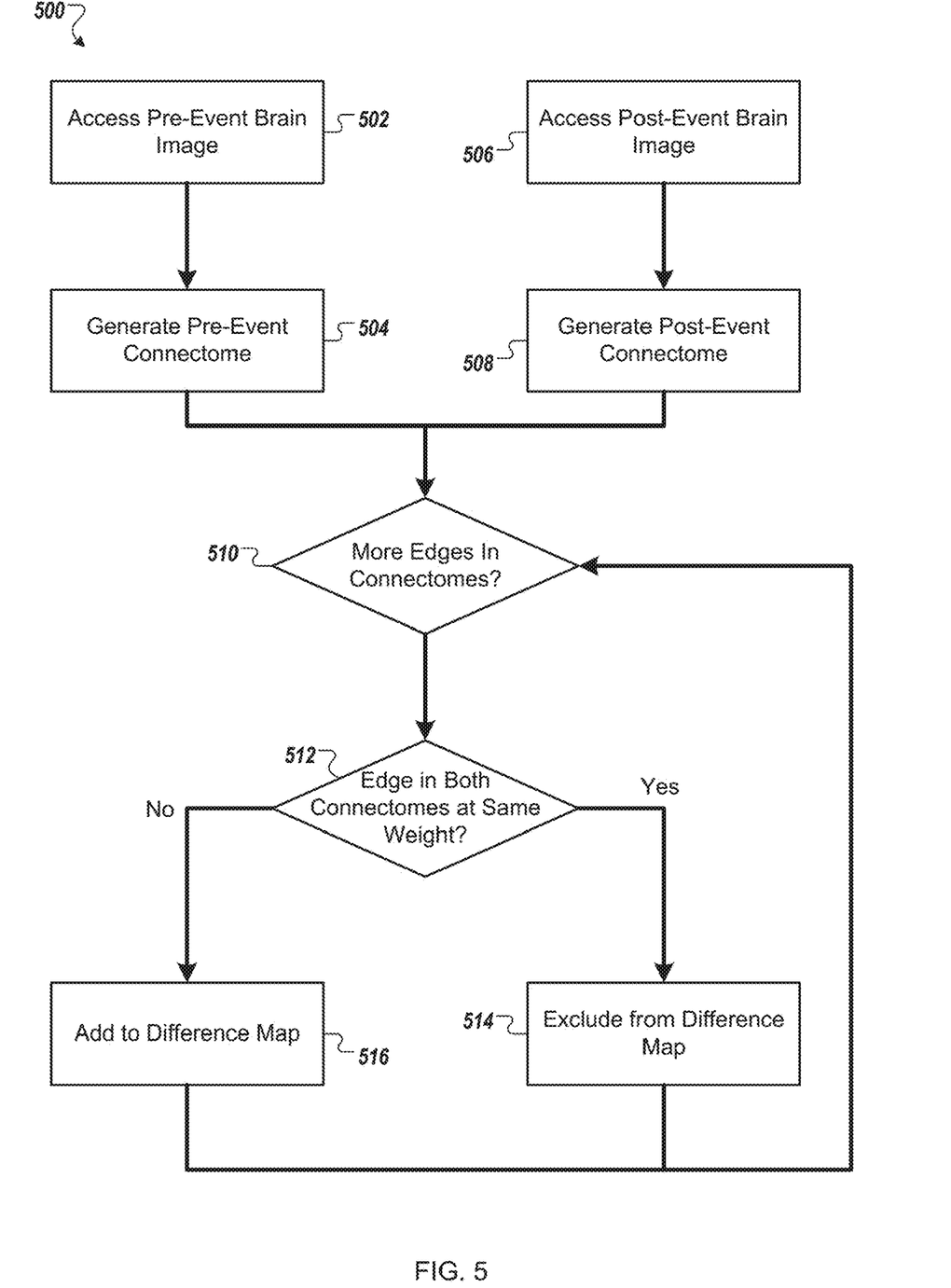
FIG. 5 shows an example process of generating a connectome-difference map from connectomes.

FIG. 5 shows an example process 500 of generating a connectome-difference map from connectomes. For example, the process 500 can be used by computing apparatus 206 in generating a connectome-difference map 416, and will be used in this description. Other systems may perform the process 500 or other processes.

The pre-event brain image is accessed 502. For example, computing apparatus 206 can receive, e.g., over a computer network, from an internal memory, or from a mountable memory, data generated by the medical imager 202 of the patient's brain before the surgery to remove the tumor.

The pre-event connectome is generated from the pre-event brain image 504. For example, computing apparatus 206 can submit the pre-event brain image to a function that receives brain images and outputs connectomes based on the input image. In some cases, computing apparatus 206 can also pre-process the input data, post-process the output data, store data, etc.

The post-event brain image is accessed 506. For example, computing apparatus 206 can receive, e.g., over a computer network, from an internal memory, or from a mountable memory, data generated by the medical imager 202 of the patient's brain after the surgery to remove the tumor.

The post-event connectome is generated from the post-event brain image 508. For example, computing apparatus 206 can submit the post-event brain image to a function that receives brain images and outputs connectomes based on the input image. As will be appreciated, this may be the same or a different function as that described above. In some cases, computing apparatus 206 can also pre-process the input data, post-process the output data, store data, etc.

Connectome edges are analyzed 510. With the pre-event difference map and the post-event difference map available, computing apparatus 206 can iterate through the connectomes to determine which edges change from pre-event connectome to post-event connectome.

While edges remain to be analyzed 510, it is determined if a given edge is in both the pre-event connectome and the post-event connectome, and if they have the same weight 512. In this example, the test for sameness can include a determination that the difference is less than a threshold value. This can allow for, for example, difference in the imaging due to biological function, imaging noise, etc. to avoid false identification of a change that is not caused by a change in the brain due to the event.

In some cases, the threshold value can be determined by finding distances from mean under Gaussian distributions of historical datasets of images or of the weights in the currently-processed dataset. Such thresholds would reflect "common" or "expected" weights of historic datasets or current data. In another example, a machine learning classifier as previously described in this document can provide the threshold value.

If the edge is found in both connectomes, and if the edge has the same weight 512, that edge can be excluded from the connectome-difference map 514. This represents an edge that did not change, or that changed less than a threshold amount, when the surgery was performed. As such, computing apparatus 206 does not record the edge in the connectome-difference map.

If the edge is not found in both connectomes, or if the edge has a different weight 512, the edge is added to the difference map. For example, computing apparatus 206 can record the edge with a weight that is the difference between the pre-event edge and post-event edge, using a weight of 0 if the edge is not present. This may result in, for example, an edge weight with a negative value if the connection was weakened or terminated by the event, and a positive value if the edge was created or strengthened by the event.

As such, by completing the process 500, computing apparatus 206 can create the connectome-difference map from a pre-event image and a post-event image. However, another process may begin with, for example a pre-event connectome and a post-event connectome. Other formats for the connectome-difference map may be used. For example, the pre-event and post-event connectome may be stored to disk in one format (e.g., a format that efficiently stores a more-populated data set such as an adjacency matrix) and the connectome-difference map may be stored to disk in a second format (e.g., a format that more efficiently stores a less-populated data set such as a linked-list of edges and weight).

Figure 6:
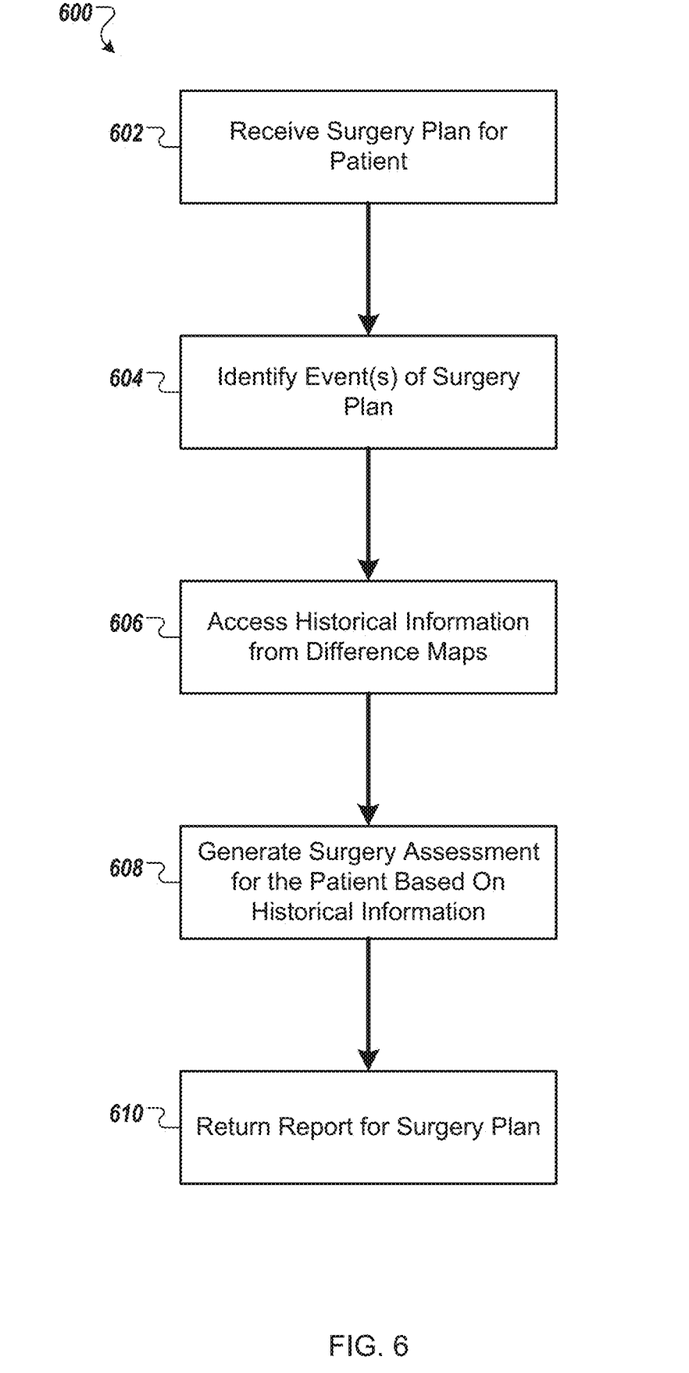
FIG. 6 shows an example process of automated surgery assessment.

FIG. 6 shows an example process 600 of automated surgery assessment. For example, the process 600 can be used by computing apparatus 206 in assessing a surgery plan, and will be used in this description. Other systems may perform the process 600 or other processes. In one example, the process 600 can be used to assess a surgery plan for tumor removal for a particular patient. The surgery plan may initially include a point-of-entry that is near the tumor, but that would require damage to a healthy network. The process 600 can identify such a state and suggest a plan that involves a lengthier traversal through the brain, but traversing through less healthy networks, resulting is better clinical outcomes for the patient overall.

A surgery plan is received 602. For example, computing apparatus 206 can receive a surgery plan for a second subject that is different than the patient described above. This surgery plan may include a plan to remove a tumor from the brain in a location that is similar, but not identical, to the tumor removed from the first patient.

Events of the surgery plan are identified 604. For example, computing apparatus 206 can identify the plan to remove the second patient's tumor, and may generate data characterizing this as an event. Computing apparatus 206 can determine that the surgery plan is a second event with at least a threshold similarity to the first event based on characteristics of the first patient's tumor removal.

Historical information from difference maps is accessed 606. For example, computing apparatus 206 may search for all records of all surgeries similar to the data about the planned surgery. Computing apparatus 206 may receive, for example, specific information about the first patient's surgery, or may receive aggregated or otherwise synthesized data. This can include machine-learning classifiers trained on a data set that includes a tagged copy of the first patient's surgery.

A surgery assessment is generated at least in part based on the historical information 608. For example, computing apparatus 206 can generate the assessment based on all returned data described above. This may include scoring similarities between the planned surgery, and identifying the most similar. This can include submitting details about the current surgery to a classifier function to receive as output a prediction about the outcome of the surgery.

The surgery plan is returned 610. For example, computing apparatus 206 can return a report for the surgery plan that includes an assessment generated, at least in part, on the connectome-difference map. This report can include suggested alterations to the plan, identification of high-risk elements of the plan, information about expected outcomes, etc.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

The invention claimed is:

1. A system for generating medical images, the system comprising:
   one or more processors; and
   computer memory storing instructions that, when executed by the one or more processors, cause the one or more processors to perform operations, comprising:
   accessing a pre-event connectome of a subject brain, wherein:
      the pre-event connectome is generated from pre-event brain image data; and
      the pre-event connectome defines i) first functional nodes in the subject brain and ii) first edges that represent connections between the first functional nodes before the subject has undergone an event;
   accessing a post-event connectome of the subject brain, wherein:
      the post-event connectome is generated from post-event brain image data; and
      the post-event connectome defines i) second functional nodes in the subject brain and ii) second edges that represent connections between the second functional nodes after the subject has undergone the event;
   generating a connectome-difference map data that records the difference between the pre-event connectome and the post-event connectome;
   rendering the connectome-difference map data with an image of the subject's brain having connections overlaid; and
   taking an action based on the connectome-difference map data.

2. The system of claim 1, wherein the first functional nodes are the same nodes as the second functional nodes.

3. The system of claim 1, wherein the first functional nodes comprise all of the second functional nodes and also comprise additions functional nodes.

4. The system of claim 1, wherein the event is at least one of the group consisting of: a surgical removal of brain tissue, a traumatic brain injury, a behavioral intervention for the subject, advancement of a medical condition that causes cognitive decline, and learning by the subject.

5. The system of claim 1, the operations further comprising:
   imaging the subject before the event to generate the pre-event brain image data;
   imaging the subject after the event to generate the post-event brain image data;
   generating the pre-event connectome from the pre-event brain image data; and
   generating the post-event connectome from the post-event brain image data.

6. The system of claim 1, wherein a first functional node and a corresponding second functional node represent the same point of brain topology, and wherein the first functional node is in a first location in a skull of the subject and the second node is in a second location in the skull of the subject do to a change in brain physiology as part of the event.

7. The system of claim 1, wherein the pre-event connectome and the post-event connectome are topologically invariant.

8. The system of claim 1, the operations further comprising generation of a proposed therapy plan for the subject based on the connectome-difference map data.

9. The system of claim 1, wherein the event is a first event and wherein the operations further comprising:
   receiving surgery-plan data for a second subject, the surgery-plan data defining at least one parameter for a surgical intervention for the second subject;
   determining that the surgical intervention is a second event with at least a threshold similarity to the first event; and
   returning a report for the surgery-plan data that includes an assessment generated, at least in part, on the connectome-difference map data.

10. The system of claim 1, wherein the event is a disease and the operations further comprise:
    generating a therapy recommendation based, at least in part, on the connectome-difference map data.

11. The system of claim 1, the operations further comprising generating report-data that includes an explanation of a change in subject health caused by the event using the connectome-difference map data.

12. A method for generating medical images, the method comprising:

accessing a pre-event connectome of a subject brain, wherein:
  the pre-event connectome is generated from pre-event brain image data; and
  the pre-event connectome defines i) first functional nodes in the subject brain and ii) first edges that represent connections between the first functional nodes before the subject has undergone an event;
accessing a post-event connectome of the subject brain, wherein:
  the post-event connectome is generated from post-event brain image data; and
  the post-event connectome defines i) second functional nodes in the subject brain and ii) second edges that represent connections between the second functional nodes after the subject has undergone the event;
generating a connectome-difference map data that records the difference between the pre-event connectome and the post-event connectome;
rendering the connectome-difference map data with an image of the subject's brain having connections overlaid; and
taking an action based on the connectome-difference map data.

13. The method of claim 12, wherein the first functional nodes are the same nodes as the second functional nodes.

14. The method of claim 12, wherein the first functional nodes comprise all of the second functional nodes and also comprise additions functional nodes.

15. The method of claim 12, wherein the event is at least one of the group consisting of: a surgical removal of brain tissue, a traumatic brain injury, a behavioral intervention for the subject, advancement of a medical condition that causes cognitive decline, and learning by the subject.

16. The method of claim 12, the method further comprising:
  imaging the subject before the event to generate the pre-event brain image data;
  imaging the subject after the event to generate the post-event brain image data;
  generating the pre-event connectome from the pre-event brain image data; and
  generating the post-event connectome from the post-event brain image data.

17. The method of claim 12, wherein a first functional node and a corresponding second functional node represent the same point of brain topology, and wherein the first functional node is in a first location in a skull of the subject and the second node is in a second location in the skull of the subject do to a change in brain physiology as part of the event.

18. Non-transitory computer-readable media tangibly storing instructions that, when executed by one or more processors, cause the one or more processors to perform operations, comprising:
  accessing a pre-event connectome of a subject brain, wherein:
    the pre-event connectome is generated from pre-event brain image data; and
    the pre-event connectome defines i) first functional nodes in the subject brain and ii) first edges that represent connections between the first functional nodes before the subject has undergone an event;
  accessing a post-event connectome of the subject brain, wherein:
    the post-event connectome is generated from post-event brain image data; and
    the post-event connectome defines i) second functional nodes in the subject brain and ii) second edges that represent connections between the second functional nodes after the subject has undergone the event;
  generating a connectome-difference map data that records the difference between the pre-event connectome and the post-event connectome;
  rendering the connectome-difference map data with an image of the subject's brain having connections overlaid; and
  taking an action based on the connectome-difference map data.

* * * * *